United States Patent
Smart

(10) Patent No.: US 9,227,033 B2
(45) Date of Patent: *Jan. 5, 2016

(54) RESPIRATORY MASK ASSEMBLY

(75) Inventor: Gregory Scott Smart, Randwick (AU)

(73) Assignee: ResMed Limited, Bella Vista (AU)

( * ) Notice: Subject to any disclaimer, the term of this patent is extended or adjusted under 35 U.S.C. 154(b) by 510 days.

This patent is subject to a terminal disclaimer.

(21) Appl. No.: 13/396,002

(22) Filed: Feb. 14, 2012

(65) Prior Publication Data

US 2012/0180794 A1  Jul. 19, 2012

Related U.S. Application Data

(60) Continuation of application No. 12/419,442, filed on Apr. 7, 2009, now Pat. No. 8,113,197, which is a continuation of application No. 11/322,237, filed on Jan. 3, 2006, now Pat. No. 7,861,714, which is a (Continued)

(30) Foreign Application Priority Data

Feb. 9, 1999  (AU) ........................ PP8550

(51) Int. Cl.
*A61M 16/06* (2006.01)
*A61M 16/08* (2006.01)
*A61M 16/20* (2006.01)

(52) U.S. Cl.
CPC .......... *A61M 16/06* (2013.01); *A61M 16/0616* (2014.02); *A61M 16/0683* (2013.01); *A61M 16/08* (2013.01); *A61M 16/208* (2013.01); *Y10S 128/912* (2013.01); *Y10T 137/7771* (2015.04)

(58) Field of Classification Search
CPC .................................................. A61M 16/06
USPC ............ 128/206.24, 206.26, 206.27, 206.28, 128/204.18, 202.27, 206.12, 206.21, 128/205.29, 205.25; 138/109, 155; 285/921, 330
See application file for complete search history.

(56) References Cited

U.S. PATENT DOCUMENTS 35,724 A  6/1862  Wilcox
463,351 A  11/1891  Elliott
(Continued)

FOREIGN PATENT DOCUMENTS

CA  88122  11/1999
DE  297 21 766 U1  3/1998
(Continued)

OTHER PUBLICATIONS

ResCare Limited, "Sullivan™ Nasal CPAP System, *Nose Mask Clip—User Instructions*", 5/90, 1pg.
ResMed, Mask Systems Product Brochure, 2 pages, Sep. 1992.
Respironics, Inc. "Nasal Mask System Silicone Contour Mask" Product Instructions, 2 pages, Jun. 1997.
Japanese Office Action English Translation for JP 2000-029094, 3 pages.

(Continued)

*Primary Examiner* — Victoria J Hicks
*Assistant Examiner* — Tarla Patel
(74) *Attorney, Agent, or Firm* — Nixon & Vanderhye P.C.

(57) ABSTRACT

A respiratory mask assembly for delivering breathable gas to a patient includes a mask frame having a first cooperating interlocking structure; a mask cushion provided to the frame; a cushion clip to retain the mask cushion on the mask frame, the cushion clip having a second cooperating interlocking structure and being selectively attachable to and detachable from the mask frame, the first and second cooperating interlocking structures interlocking to secure the cushion clip on the mask frame; and an elbow joint provided to the frame and having a swivel tube adapted to connect to a gas delivery conduit. The first and second cooperating interlocking structures include a tab-recess arrangement in which a plurality of tabs are engageable within respective recesses.

25 Claims, 3 Drawing Sheets

Related U.S. Application Data continuation of application No. 10/164,370, filed on Jun. 10, 2002, now Pat. No. 7,207,334, which is a division of application No. 09/498,705, filed on Feb. 7, 2000, now Pat. No. 6,491,034.

(56) References Cited

U.S. PATENT DOCUMENTS

| | | |
|---|---|---|
| 715,611 A | 12/1902 | Schenker et al. |
| 716,530 A | 12/1902 | Giddens |
| 812,706 A | 2/1906 | Warbasse |
| 1,333,075 A | 3/1920 | Hill et al. |
| 1,381,826 A | 6/1921 | Hansen |
| 1,653,572 A | 12/1927 | Jackson |
| 1,672,165 A | 6/1928 | Lewis |
| 1,733,020 A | 10/1929 | Jones |
| 2,029,129 A | 1/1936 | Schwartz |
| 2,033,448 A | 3/1936 | James |
| 2,141,222 A | 12/1938 | Pioch |
| 2,359,506 A | 10/1944 | Battley et al. |
| 2,371,965 A | 3/1945 | Lehmberg |
| 2,454,103 A | 11/1948 | Swidersky |
| 2,638,161 A | 5/1953 | Jones |
| 2,823,671 A | 2/1958 | Garelick |
| 2,832,015 A | 4/1958 | Ortega |
| 2,893,387 A | 7/1959 | Gongoll et al. |
| 2,931,356 A | 4/1960 | Schwarz |
| 3,141,213 A | 7/1964 | Nicholas |
| 3,189,027 A | 6/1965 | Bartlett, Jr. |
| 3,474,783 A | 10/1969 | Ulmann |
| 3,494,072 A | 2/1970 | Olson |
| 3,523,534 A | 8/1970 | Nolan |
| 3,535,810 A | 10/1970 | Baehrle |
| 3,555,752 A | 1/1971 | Bogaert |
| 3,824,999 A | 7/1974 | King |
| 4,049,357 A | 9/1977 | Hamisch, Jr. |
| 4,064,875 A | 12/1977 | Cramer et al. |
| 4,111,197 A | 9/1978 | Warncke et al. |
| 4,121,580 A | 10/1978 | Fabish |
| 4,164,942 A | 8/1979 | Beard et al. |
| 4,226,234 A | 10/1980 | Gunderson |
| 4,274,404 A | 6/1981 | Molzan et al. |
| 4,380,102 A | 4/1983 | Hansson |
| 4,494,538 A | 1/1985 | Ansite |
| 4,506,665 A | 3/1985 | Andrews et al. |
| 4,549,334 A | 10/1985 | Miller |
| 4,580,556 A | 4/1986 | Kondur |
| 4,606,340 A | 8/1986 | Ansite |
| 4,622,964 A | 11/1986 | Flynn |
| 4,633,972 A | 1/1987 | DeRocher |
| 4,783,029 A | 11/1988 | Geppert et al. |
| 4,794,921 A | 1/1989 | Lindkvist |
| 4,807,617 A | 2/1989 | Nesti |
| 4,809,692 A | 3/1989 | Nowacki et al. |
| 4,835,820 A | 6/1989 | Robbins, III |
| 4,841,953 A | 6/1989 | Dodrill |
| 4,870,963 A | 10/1989 | Carter |
| 4,875,714 A | 10/1989 | Lee |
| 4,898,174 A | 2/1990 | Fangrow, Jr. |
| 4,899,614 A | 2/1990 | Kataumi |
| 4,974,586 A | 12/1990 | Wandel et al. |
| 4,981,134 A | 1/1991 | Courtney |
| 4,997,217 A | 3/1991 | Kunze |
| 5,003,633 A | 4/1991 | Itoh |
| 5,005,568 A | 4/1991 | Loescher et al. |
| 5,062,420 A * | 11/1991 | Levine ............ 128/204.18 |
| 5,080,094 A | 1/1992 | Tayebi |
| 5,136,760 A | 8/1992 | Sano et al. |
| 5,215,336 A | 6/1993 | Worthing |
| 5,243,971 A * | 9/1993 | Sullivan et al. ........ 128/205.25 |
| 5,253,641 A | 10/1993 | Choate |
| 5,311,862 A | 5/1994 | Blasdell et al. |
| 5,398,673 A | 3/1995 | Lambert |
| 5,438,981 A | 8/1995 | Starr et al. |
| 5,501,214 A | 3/1996 | Sabo |
| 5,538,001 A | 7/1996 | Bridges |
| 5,645,049 A | 7/1997 | Foley et al. |
| 5,647,355 A | 7/1997 | Starr et al. |
| 5,676,133 A | 10/1997 | Hickle et al. |
| 5,709,204 A | 1/1998 | Lester |
| 5,724,965 A | 3/1998 | Handke et al. |
| 5,794,617 A | 8/1998 | Brunell et al. |
| 5,839,436 A | 11/1998 | Fangrow et al. |
| 5,860,677 A | 1/1999 | Martins et al. |
| 5,896,857 A | 4/1999 | Hely et al. |
| 5,909,732 A | 6/1999 | Diesel et al. |
| 5,921,239 A | 7/1999 | McCall et al. |
| 5,937,851 A | 8/1999 | Serowski et al. |
| 5,979,025 A | 11/1999 | Horng |
| 6,006,748 A | 12/1999 | Hollis |
| D428,139 S | 7/2000 | Smart |
| 6,082,360 A | 7/2000 | Rudolph et al. |
| D428,988 S | 8/2000 | Smart |
| D430,663 S | 9/2000 | Smart |
| 6,119,693 A | 9/2000 | Kwok et al. |
| 6,189,532 B1 | 2/2001 | Hely et al. |
| 6,192,886 B1 | 2/2001 | Rudolph |
| 6,196,223 B1 | 3/2001 | Belfer et al. |
| D443,355 S | 6/2001 | Gunaratnam et al. |
| 6,240,605 B1 | 6/2001 | Stevens et al. |
| 6,250,375 B1 | 6/2001 | Lee et al. |
| 6,256,846 B1 | 7/2001 | Lee |
| 6,272,722 B1 | 8/2001 | Lai |
| 6,321,421 B1 | 11/2001 | Lim |
| 6,381,813 B1 | 5/2002 | Lai |
| 6,412,487 B1 | 7/2002 | Gunaratnam et al. |
| 6,449,817 B1 | 9/2002 | Hsu |
| 6,463,931 B1 | 10/2002 | Kwok et al. |
| 6,491,034 B1 | 12/2002 | Gunaratnam et al. |
| 6,513,206 B1 | 2/2003 | Banitt et al. |
| 6,513,526 B2 | 2/2003 | Kwok et al. |
| 6,520,182 B1 | 2/2003 | Gunaratnam |
| 6,532,961 B1 | 3/2003 | Kwok et al. |
| 6,615,832 B1 | 9/2003 | Chen |
| 6,796,308 B2 | 9/2004 | Gunaratnam et al. |
| 7,207,334 B2 * | 4/2007 | Smart ............ 128/206.24 |
| 7,861,714 B2 * | 1/2011 | Smart ............ 128/204.18 |
| 2002/0023649 A1 | 2/2002 | Gunaratnam et al. |
| 2002/0023650 A1 | 2/2002 | Gunaratnam et al. |
| 2002/0153012 A1 | 10/2002 | Gunaratnam et al. |
| 2002/0174868 A1 | 11/2002 | Kwok et al. |
| 2003/0005935 A1 | 1/2003 | Kwok et al. |
| 2004/0134497 A1 | 7/2004 | Gunaratnam et al. |
| 2006/0130843 A1 | 6/2006 | Gunaratnam et al. |

FOREIGN PATENT DOCUMENTS

| | | |
|---|---|---|
| DE | 499 00 269.5 | 1/1999 |
| EP | 1 027 905 A3 | 8/2000 |
| ES | 145309 | 1/2000 |
| FR | 2 691 906 | 12/1993 |
| FR | 99/16 | 8/1999 |
| GB | 2080119 | 12/1998 |
| GB | 2080120 | 12/1998 |
| GB | 2080121 | 12/1998 |
| JP | 48-55696 | 10/1971 |
| JP | 59-55535 | 4/1984 |
| JP | 61-67747/86 | 5/1986 |
| JP | 7-21058/95 | 4/1995 |
| JP | 7-308381 | 11/1995 |
| JP | 9-501084 | 2/1997 |
| JP | 1105649 | 2/1999 |
| SE | 65481 | 8/2000 |
| WO | WO 80/01645 | 8/1980 |
| WO | WO 87/01950 | 4/1987 |
| WO | WO 95/04566 | 2/1995 |
| WO | WO 98/26830 | 6/1998 |

(56) References Cited

FOREIGN PATENT DOCUMENTS

| WO | WO 98/48878 | 11/1998 |
| WO | WO 99/30760 | 6/1999 |
| WO | WO 00/38772 | 7/2000 |

OTHER PUBLICATIONS

Office Action mailed Nov. 22, 2012 in Canadian Application No. 2,733,839 (2 pages).
The American Heritage Dictionary, Second College Edition, 1982, 3 pages.

* cited by examiner

RESPIRATORY MASK ASSEMBLY

CROSS-REFERENCES TO RELATED APPLICATIONS

This application is a continuation of U.S. application Ser. No. 12/419,442, filed Apr. 7, 2009 (now U.S. Pat. No. 8,113, 197), which is a continuation of U.S. application Ser. No. 11/322,237, filed Jan. 3, 2006, now U.S. Pat. No. 7,861,714, which is a continuation of U.S. application Ser. No. 10/164, 370, filed Jun. 10, 2002, now U.S. Pat. No. 7,207,334, which is a divisional of U.S. application Ser. No. 09/498,705, filed Feb. 7, 2000, now U.S. Pat. No. 6,491,034, and related to the following applications: U.S. application Ser. No. 09/985,457, filed Nov. 2, 2001, now U.S. Pat. No. 7,185,652, and U.S. application Ser. No. 09/985,458, filed Nov. 2, 2001, now U.S. Pat. No. 7,089,939, and U.S. application Ser. No. 11/285,077, now U.S. Pat. No. 7,174,893, each incorporated herein by reference in its entirety.

FIELD OF THE TECHNOLOGY

The present technology relates to improvements in patient gas delivery apparatus of the kind used in the analysis and treatment of respiratory disorders. The invention will be described with particular reference to patient gas delivery apparatus used in the treatment of respiratory disorders such as Obstructive Sleep Apnea (OSA) but it is not intended to be limited thereto.

BACKGROUND OF THE TECHNOLOGY

Patient gas delivery apparatus of the kind having a mask worn by a patient and a gas delivery conduit attached to the mask are commonly used in the analysis and treatment of respiratory disorders. The gas conduit delivers a gas under pressure to the patient. It is necessary that the gas conduit is detachable from the mask to facilitate cleaning.

Patient gas delivery apparatus typically includes at a minimum, a gas delivery conduit and a nose or full face mask. In some cases it is a clinical requirement that additional components be included, such as means for $CO_2$ washout, for example, vents, anti-asphyxia valves and the like. In some cases, these additional components must be assembled in between the gas delivery conduit and the mask. Problems with prior art assemblies include: (a) they may be inadvertently assembled without the additional components; (b) they may be incorrectly assembled, for example, incorrectly aligned; (c) during the course of treatment, the patient may inadvertently remove or dismantle the assembly and incorrectly reassemble it.

Further, known mask cushions are usually molded from a relatively soft, resilient, elastic material and they are shaped during manufacture to match the facial contours of an average intended wearer. However, a problem with the known types of masks is that, because individuals vary so much from the average, the masks must be forced against their inherent resiliency to deform and so adapt to the shapes of the users in order to avoid gas leakage. This requires that the masks be secured firmly by retaining straps or harnesses in order to prevent air leakage.

Flow generators are typically utilized to deliver a breathable gas (i.e., air) to a patient wearing the mask. In CPAP treatment, gas is delivered to the patient's airways at about 2-30 cm $H_2O$ above atmospheric pressure. The flow generator is generally connected to flexible tubing which is secured to the mask worn by the patient. If the flow generator's operation is interrupted as a result of a power outage or other mechanical or electrical failure, there may be a significant build up of carbon dioxide in the mask as the patient's exhaled air is not washed out of outlet vents which are usually contained in the mask. This may present a health problem to the patient.

There have been numerous patents which have addressed some sort of safety valve for gas or air delivery masks. An example of such a patent is U.S. Pat. No. 5,438,981. This patent discloses a counter balanced, rigid valve element which depending on the gas flow, either covers an opening to the ambient air or covers the gas flow airway such that the air or breathing gas is forced out into the ambient air opening However, this system suffers from being a fairly complicated and expensive system whose correct operation relies on a counter balanced moving part moving relative to its housing. Further, if any condensation from the air gets on or around the balanced valve element, the operation of this valve element can be compromised. This valve is also difficult to clean.

Applicant's International Application PCT/AU97/00849 discloses a valve having a single valve element. However, whilst being simpler than preceding valves of this type, the valve shown in PCT/AU97/00849 still relies on the use of a rigid valve element moving relative to its housing and biased by magnets.

SUMMARY OF THE INVENTION

One aspect of the present invention is directed towards solving or ameliorating one or more of these problems. One aspect of the invention will be described with reference to a full face mask, though other forms of mask and additional components may be used.

According to one example, a respiratory mask assembly for delivering breathable gas to a patient comprises a mask frame having a first cooperating interlocking structure; a mask cushion provided to the frame and adapted to form a seal on the patient's face; a cushion clip to retain the mask cushion on the mask frame, the cushion clip having a second cooperating interlocking structure and being selectively attachable to and detachable from the mask frame, the first and second cooperating interlocking structures interlocking with one another in a cooperating relationship to secure the cushion clip on the mask frame; and an elbow joint provided to the frame and having a swivel tube adapted to connect to a gas delivery conduit, wherein the first and second cooperating interlocking structures are provided to at least a bottom and left and right sides of the mask frame and cushion clip, and include a tab-recess arrangement in which a plurality of tabs are engageable within respective recesses in interlocking relation to secure the clip to the frame.

According to another example, a respiratory mask assembly for delivering breathable gas to a patient comprises a mask frame having a first cooperating interlocking structure; a cushion clip having a second cooperating interlocking structure and being selectively attachable to and detachable from the mask frame, the first and second cooperating interlocking structures interlocking with one another in a cooperating relationship to secure the cushion clip on the mask frame; and a mask cushion adapted to form a seal on the patient's face and having an outer peripheral portion positioned between the mask frame and the cushion clip so as to seal the mask cushion on the mask frame.

According to yet another example, a respiratory mask assembly for delivering breathable gas to a patient comprises a mask frame; a mask cushion adapted to form a seal with the patient's face; and a clip member engaged with the mask cushion and structured to interlock with the mask frame, wherein the mask frame and the clip member include a tab-recess arrangement in which a plurality of securing tabs engage with a corresponding one of a plurality of recesses so as to retain the mask cushion on the mask frame, the tab-recess arrangement provided to at least a bottom and left and right sides of the mask frame and clip member.

These and other aspects of the invention will be described in or apparent from the following detailed description.

BRIEF DESCRIPTION OF THE DRAWINGS

Further examples of the present technology will now be described by way of example only with reference to the accompanying drawings in which.

DETAILED DESCRIPTION

Figure 1:
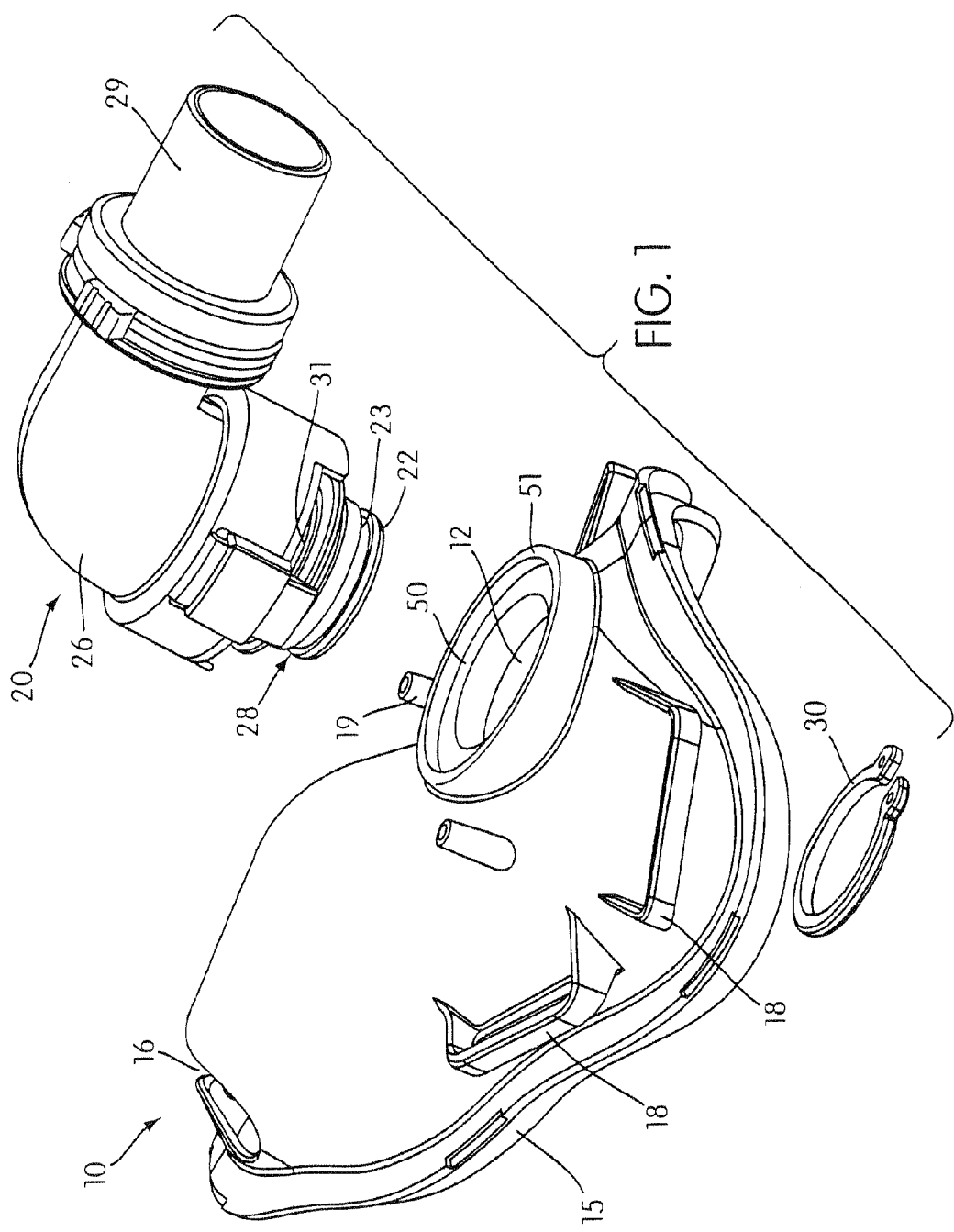
FIG. 1 is a perspective view showing the mask, anti-asphyxia valve housing and conduit connection assembly.

In FIG. 1 a mask frame is shown generally at 10. The mask is designed to be worn on a patient's face and is secured by means of straps (not shown) received by attachment points 18.

A conduit end assembly is shown generally at 20, including an elbow part 26 having at one end thereof a combined vent/connector piece 28. The elbow and vent/connector piece together form a housing for an anti-asphyxia valve (as will be further discussed) or other internal components (not shown). At the other end of the elbow is a detachable swivel tube 29 for connection of the gas delivery conduit (not shown).

The mask 10 includes a circular aperture 12 sized to receive a mating portion 22 of the vent/connector piece 28. The mating portion 22 has an annular groove 23 formed therein that receives a locking means 30 in the form of a C-shaped clip attached after mating to the mask. The clip 30 has an outside diameter greater than the width of the aperture 12 and an inner diameter adapted to ensure a snug fit within the annular groove 23. The clip 30 is resilient and can expand sufficiently to allow the clip to be fitted into and removed from the groove 23. As shown in FIG. 1, the clip 30 is located onto the mating portion 22 on the inside of the mask 10. In this position, the clip 30 is inaccessible while the mask is being worn by a patient. Once the mating portion 22 of the vent/connector piece 28 has been inserted through the aperture 12 and the locking clip placed in the annular groove, the conduit end assembly 20 and the mask 10 cannot be separated without first removing the mask from the patient.

Figure 2:
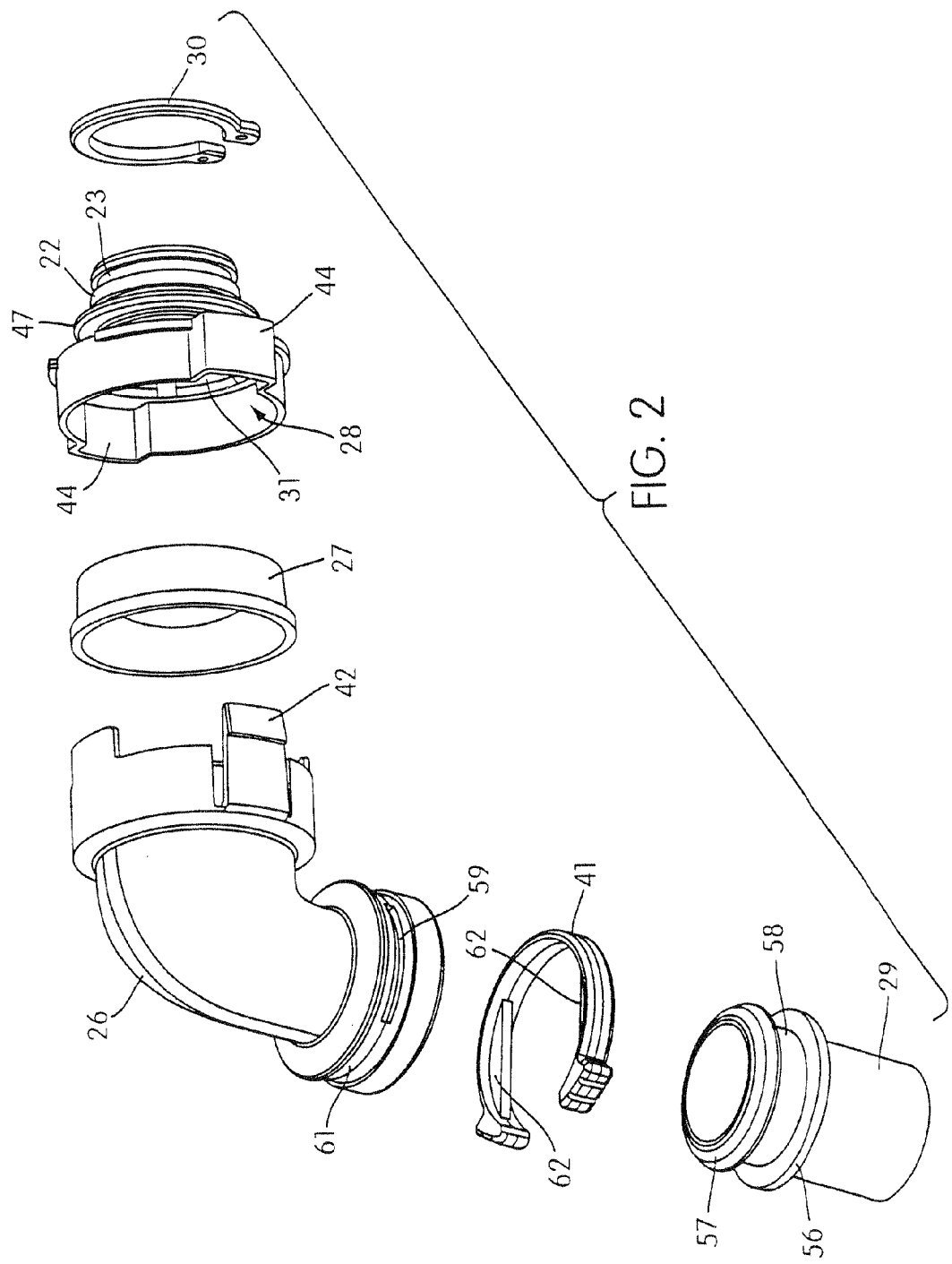
FIG. 2 is an exploded view of the anti-asphyxia valve and conduit connection assembly shown in FIG. 1.

An exploded view of one embodiment of the anti-asphyxia valve and conduit connector assembly is shown in FIG. 2.

As illustrated in FIG. 2, the end of the elbow 26 adjacent the mask 10 is fitted with an anti-asphyxia valve arrangement that provides an air passage to the patient in the event of failure of the gas delivery apparatus, consisting of a valve membrane 27 fitted into the end of elbow 26 and vents 31 in the vent/connector piece 28. During proper operation of the gas delivery system, the valve membrane remains in the orientation shown in FIG. 2, closing off the vents 31. In the event of a drop in pressure below a predetermined level, the valve membrane 27 flips to a reverse orientation, opening the vents 31. The construction and operation of the anti-asphyxia valve is described in more detail in the Applicant's Australian Patent Application No. 65527/99, the contents of which are incorporated herein by reference and described herein.

Resilient detents 42 on the elbow 26 pass through and engage behind slot-forming formations 44 in the vent/connector piece 28 to provide releasable engagement of the two parts.

The vent/connector piece has a collar 47 that abuts a corresponding surface of the mask 10 to limit the distance that the vent/connector piece can be inserted into the mask aperture 12 (FIG. 1). The corresponding surface is an annulus 50 having a protruding rim 51 the outer circumference of which preferably engages the inner surface of the detents 42 on insertion of the mating portion 22 into the aperture 12. This engagement prevents the detents from being pushed radially inwards sufficiently for the detents to disengage from behind the slot-forming formations 44, thus preventing the elbow 26 and vent/connector piece 28 from separating whilst still attached to the mask frame 11, for example during patient treatment. The result of this is that the anti-asphyxia valve arrangement cannot be disassembled without first removing the elbow and vent/connector piece assembly from the mask. However, once disconnected from the mask, the assembly may be readily separated for cleaning and then reassembled.

The other, distal end of elbow 26 has an enlarged diameter portion which receives the swivel tube 29, onto which a flexible gas conduit (not shown) may be fitted. The swivel tube 29 has a pair of flanges 56 and 57 defining an annular groove 58 therebetween. The end of swivel tube 29 is inserted into the elbow 26 until the end flange 57 abuts an inner surface (not shown) within elbow 26. In this position the annular groove 58 is at least partially aligned with an annular groove 61 in the exterior of the elbow, which receives a swivel clip 41.

The swivel clip 41 has an inner diameter only slightly greater than the diameter of the groove 61, to ensure a snug fit within the groove. The clip 41 is resilient to permit sufficient expansion for attachment and removal of the clip from the groove. The groove 61 has slots 59 which receive lugs 62 on the clip. These lugs rotatably engage in the groove 58 between flanges 56 and 57 of the swivel tube. The swivel tube arrangement thus acts as a rotatable coupling between the conduit and the elbow whilst allowing quick attachment and removal of the gas conduit from the elbow regardless of whether the assembly is attached to the mask at the time.

Figure 3:
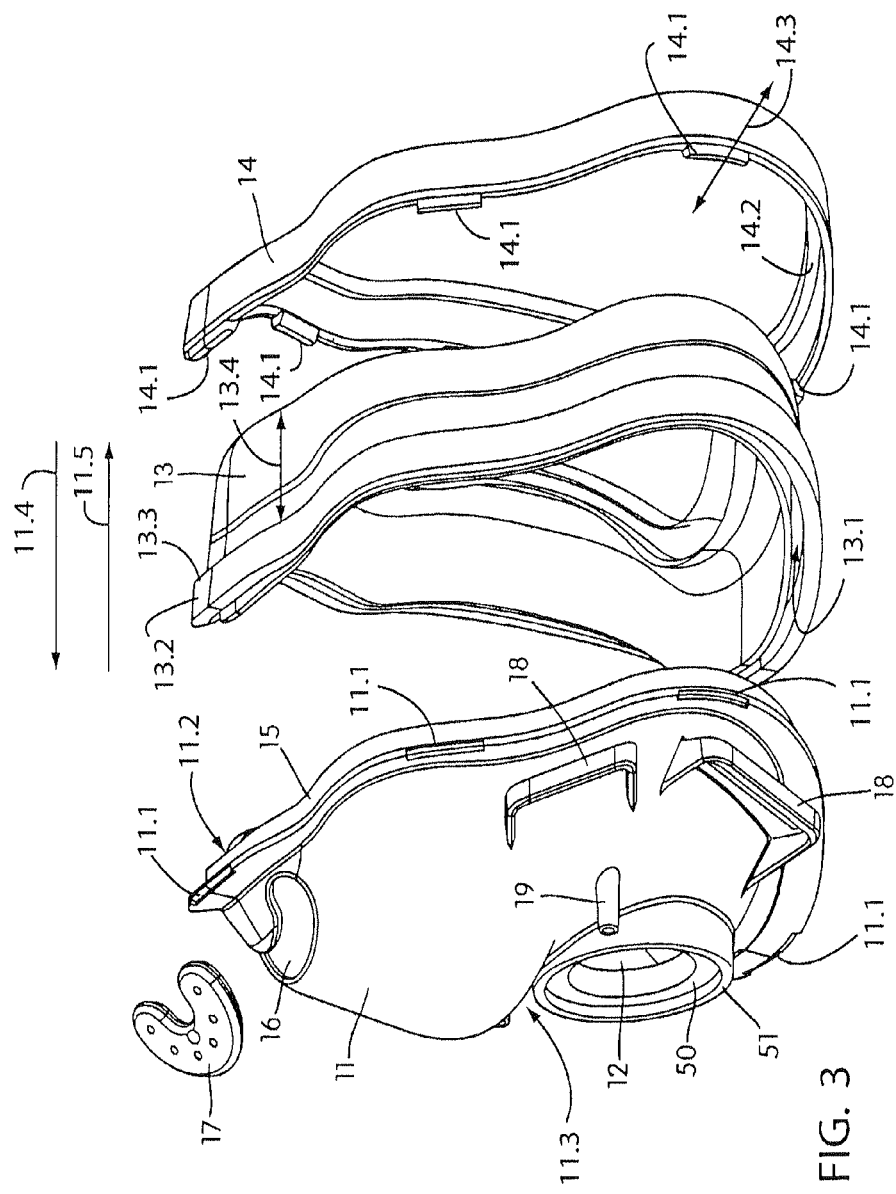
FIG. 3 is an exploded view of the mask assembly shown in FIG. 1.

As shown in FIG. 3, the mask includes a mask frame 11, cushion 13 and cushion clip 14. The cushion is received on a rib 15 extending around the periphery of the mask frame 11. The cushion is held to the rib by the cushion clip 14. The mask frame includes attachment points 18 that receive straps (not shown) for attaching the mask to the patient, an aperture 16 for receiving an air vent 17, and measurement ports 19.

The mask frame 11 includes a plurality of recesses 11.1 that provide a first cooperating interlocking structure and the cushion clip 14 includes a plurality of tabs 14.1 that is equal to a number of recesses in the mask frame 11 and provides a second cooperating interlocking structure. The plurality of tabs 14.1 engage a respective recess 11.1 to secure the cushion clip 14 on the mask frame 11.

The mask assembly, in the example shown in FIG. 3, is a full face mask. As shown in FIG. 3, the frame includes top and bottom recesses, two left side recesses and two right side recesses (not shown). The cushion clip 14 includes corresponding top and bottom tabs 14.1 as well as two right side tabs (both shown) and two left side tabs (only one shown).

The mask cushion includes a groove 13.1 extending around the periphery thereof and the groove of the cushion receives the rib 15 of frame 11.

The cushion 13 includes an outwardly extending portion 13.2 that provides the groove 13.1 on one side thereof An opposite side of the outwardly engaging portion 13.2 provides a shoulder 13.3 that engages a flange 14.2 on the cushion clip 14 to retain the cushion 13 on frame 11.

The cushion includes a rearwardly extending portion designated by reference number 13.4. The cushion serves to seal the mask assembly on the patient's face, and is structured to space the mask frame 11 from the patient's face.

The frame 11 includes a first side 11.2 structured to accommodate cushion 13, and a second side 11.3. The cushion clip 14 and frame 11 are configured to cooperate with one another such that the cushion clip 14 is selectively attachable to the frame 11 in a first direction 11.4 defined generally from the first side 11.2 to the second side 11.3 of the frame, to thereby secure the cushion 13 between the cushion clip 14 and the frame 11.

The cushion clip 14 and frame 11 are configured to cooperate with one another such that the cushion clip is selectively detachable from the frame 11 in a second direction 11.5, opposite to the first direction 11.4, defined generally from the second side 11.3 to the first side 11.2 of the frame 11, to thereby allow removal of the cushion 13 from frame 11.

Each tab 14.1 is resiliently movable in a third direction 14.3 that is substantially transverse to the first and second directions 11.4 and 11.5. Tab portions 14.1 move in the direction indicated by arrows 14.3 when the tab portions are snapped or flexed into place within recesses 11.1, and when they are removed therefrom.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A patient interface for delivering breathable gas to a patient, comprising:
    a frame having a first cooperating interlocking structure;
    a cushion provided to the frame and adapted to form a seal on the patient's face;
    a cushion clip to retain the cushion on the frame, the cushion clip having a second cooperating interlocking structure and being selectively attachable to and detachable from the frame, the first and second cooperating interlocking structures interlocking with one another in a cooperating relationship to secure the cushion clip on the frame;
    an elbow joint provided to the frame and having a swivel tube adapted to connect to a gas delivery conduit; and
    wherein the first and second cooperating interlocking structures are provided to at least a bottom and left and right sides of the frame and cushion clip, and wherein a tab-recess arrangement of the frame and cushion clip includes a plurality of tabs engageable within respective recesses to secure the clip to the frame.

2. A patient interface according to claim 1, wherein each tab is engageable within a respective recess with a snap fit.

3. A patient interface according to claim 1, wherein each tab is resiliently movable.

4. A patient interface according to claim 1, wherein the cushion includes an outwardly extending portion received on a rib extending around the periphery of the frame.

5. A patient interface according to claim 4, wherein the outwardly extending portion is held to the rib by the cushion clip.

6. A patient interface according to claim 1, further comprising a pair of upper attachment points provided to an upper portion of the frame and pair of lower attachment points provided to a lower portion of the frame, the upper and lower attachment points adapted to receive respective straps to secure the patient interface in position on the patient's face.

7. A patient interface according to claim 1, wherein the cushion includes a rearwardly extending portion structured to space the frame from the patient's face.

8. A patient interface according to claim 1, wherein the frame includes a first side structured to accommodate the cushion, and a second side, opposite the first side, and wherein the cushion clip and frame are configured to cooperate with one another such that the cushion clip is selectively attachable to the frame in a first direction defined generally from the first side to the second side of the frame, to thereby secure the cushion between the cushion clip and the frame.

9. A patient interface according to claim 8, wherein the cushion clip and frame are configured to cooperate with one another such that the cushion clip is selectively detachable from the frame in a second direction, opposite the first direction, defined generally from the second side to the first side of the frame, to thereby allow removal of the cushion from the frame.

10. A patient interface according to claim 1, wherein the first and second cooperating interlocking structures are engagable when the cushion clip is moved in a first direction defined generally from a first side of the frame that supports the cushion towards a second side of the frame opposite the first side, to thereby secure the cushion to the frame.

11. A patient interface according to claim 10, wherein the first and second cooperating interlocking structures are disengagable when the cushion clip is moved in a second direction defined generally from the second side towards the first side of the frame, to thereby allow removal of the cushion from the frame.

12. A respiratory mask assembly according to claim 1, wherein the recesses are configured to displace the respective tabs as the tabs are inserted into the recesses.

13. A respiratory mask assembly according to claim 1, wherein each tab and each recess has a unique combination of orientation and shape so that the frame and the cushion clip are securable to each other in only one orientation.

14. A respiratory mask assembly for delivering breathable gas to a patient, comprising:
    a mask frame having a first cooperating interlocking structure;
    a cushion clip having a second cooperating interlocking structure and being selectively attachable to and detachable from the mask frame, the first and second cooperating interlocking structures interlocking with one another in a cooperating relationship to secure the cushion clip on the mask frame; and
    a mask cushion adapted to form a seal on the patient's face and having an outer peripheral portion positioned between the mask frame and the cushion clip so as to seal the mask cushion on the mask frame.

15. A respiratory mask assembly according to claim 14, wherein the first and second cooperating interlocking structures include a tab-recess arrangement in which a plurality of tabs are engageable within respective recesses to secure the clip on the frame.

16. A respiratory mask assembly according to claim 14, wherein the first and second cooperating interlocking structures are provided to at least a bottom and left and right sides of the mask frame and cushion clip.

17. A respiratory mask assembly according to claim 15, wherein each tab is engageable within a respective recess with a snap fit.

18. A respiratory mask assembly for delivering breathable gas to a patient, comprising:
a mask frame;
a mask cushion adapted to form a seal with the patient's face; and
a clip member engaged with the mask cushion and structured to interlock with the mask frame,
wherein the mask frame and the clip member include a tab-recess arrangement in which a plurality of securing tabs on the clip member engage with a corresponding one of a plurality of recesses on the mask frame so as to retain the mask cushion on the mask frame, the tab-recess arrangement provided to at least a bottom and left and right sides of the mask frame and clip member.

19. The respiratory mask according to claim 18, wherein each of said securing tabs is resiliently movable.

20. A respiratory mask assembly according to claim 18, wherein each tab is engageable within a respective recess with a snap fit.

21. A respiratory mask assembly according to claim 18, wherein:
the mask frame comprises a rearwardly projecting rib adapted to engage the cushion and the cushion is held against the rib by the clip member,
the portion of the tab-recess arrangement provided on the mask frame is positioned closer to a periphery of the mask frame than the rib,
the cushion is configured so that when the clip member is attached to the mask frame, a first portion of the cushion is positioned between the clip member and the mask frame and the clip member is positioned between the mask frame and a second portion of the cushion,
the rib projects beyond the portion of the tab-recess arrangement provided on the mask frame,
the cushion comprises a flange that engages the clip member to retain at least a portion of the cushion on the clip member,
the mask assembly further comprises an elbow joint provided to the frame,
the mask frame comprises a circular aperture that receives a mating portion of the elbow joint,
the rib at least partially surrounds the circular aperture,
the cushion is configured so that when the clip member is attached to the mask frame, a first portion of the cushion is positioned between the clip member and the mask frame and the clip member is positioned between the mask frame and a second portion of the cushion,
the elbow joint comprises a collar that abuts a corresponding surface of the mask frame and limits a distance that the elbow joint can be inserted into the circular aperture,
a distal end of the elbow joint has an enlarged diameter and engages a swivel tube that is adapted to connect to a gas delivery conduit,
the mask frame comprises a vent positioned above the circular aperture, and
the cushion comprises a shoulder that engages the clip member to retain at least a portion of the cushion on the clip member.

22. A respiratory mask assembly according to claim 21, wherein the mask frame and the clip member are configured so that movement of the clip member toward the mask frame in a first direction facilitates securing the clip member to the mask frame, and the tabs are configured to move in a second direction transverse to the first direction when the clip member is assembled to the mask frame.

23. A respiratory mask assembly according to claim 22, wherein the shoulder of the cushion engages a flange of the clip member to retain at least a portion of the cushion on the clip member.

24. A respiratory mask assembly according to claim 23, wherein the clip member and the cushion are separate components.

25. A respiratory mask assembly according to claim 18, wherein the recesses are configured to displace the respective tabs as the tabs are inserted into the recesses.

* * * * *